United States Patent [19]

White

[11] Patent Number: 4,781,675

[45] Date of Patent: Nov. 1, 1988

[54] INFUSION CANNULA

[76] Inventor: Thomas C. White, 1701 S. Minnesota Ave., Sioux Falls, S. Dak. 57105-1765

[21] Appl. No.: 93,067

[22] Filed: Aug. 27, 1987

Related U.S. Application Data

[63] Continuation of Ser. No. 802,517, Nov. 27, 1985, abandoned.

[51] Int. Cl.$^4$ ............................................. A61M 27/00
[52] U.S. Cl. ....................................... 604/10; 604/247
[58] Field of Search ........................................ 623/4–6; 604/8–10, 30, 31, 49114 51, 247, 893

[56] References Cited

U.S. PATENT DOCUMENTS

| 2,969,066 | 1/1961 | Holder et al. | 604/9 |
|---|---|---|---|
| 3,452,757 | 7/1969 | Ames | 128/350 |
| 3,788,327 | 1/1974 | Donowitz et al. | 604/247 |
| 3,827,439 | 8/1974 | Schulte et al. | 128/350 |
| 4,019,514 | 4/1977 | Banko | 604/31 |
| 4,041,947 | 8/1977 | Weiss et al. | 604/51 |
| 4,078,564 | 3/1978 | Spina et al. | 604/51 |
| 4,240,434 | 12/1980 | Newkirk | 604/9 |
| 4,300,557 | 11/1981 | Refojo et al. | 604/49 |
| 4,405,316 | 9/1983 | Mittleman | 604/86 |
| 4,447,224 | 5/1984 | DeCant, Jr. | 604/67 |
| 4,452,600 | 6/1984 | Schachar | 604/51 |
| 4,464,168 | 8/1984 | Redmond et al. | 604/9 |
| 4,554,918 | 11/1985 | White | 604/10 |

FOREIGN PATENT DOCUMENTS 83304366  3/1984  European Pat. Off. .

OTHER PUBLICATIONS

Miki et al, "A Method for Chronic Drug Infusion into the Eye", 28, Jpn. J. Ophthalmol., 140–146 (1984).
Eliason et al, "An Ocular Perfusion System", Invest. Ophthalmol. Vis. Sci., 102–105 (Jan. 1980).
Michelson et al, "Experimental Endophthalmitis Treated with an Implantable Osmotic Minipump", 97, Arch. Ophthalmol., 1345–46 (Jul. 1979).
Miki et al, "Intraocular Cannula for Continuous, Chronic Drug Delivery", 103, Arch. Ophthalmol., 712–717 (May 1985).

Primary Examiner—John D. Yasko
Attorney, Agent, or Firm—Mary P. Bauman; Gregory P. Kaihoi

[57] ABSTRACT

The disclosure relates to an infusion cannula for infusing fluids into various cavities of the eye. The cannula comprises a tube having first and second ends and a check valve therebetween for allowing fluid flow only toward the first end. The first end of the cannula secured within the eye and the second end of the cannula is attached to a fluid source.

14 Claims, 2 Drawing Sheets

INFUSION CANNULA

This application is a continuation of application Ser. No. 802,517, filed 11/27/85 now abandoned.

FIELD OF THE INVENTION

This invention relates to an infusion cannula for use in delivering fluids, such as drugs, to cavities in the eye.

BACKGROUND OF THE INVENTION

In a variety of medical procedures, treatments, and research, it is desirable to provide repeated but intermittant drug delivery into the eye or into other spaces within the orbit of the eye. In the past such techniques have involved the implanting of osmotic mini-pumps attached to silastic tubing implanted in the eye, See, e.g., Miki, "A Method for Chronic Drug Infusion into the Eye", 28 *Jap. J. of Ophthalmol.*, 140 (1984); Eliason, "An Ocular Perfusion System," 19 *Invest. Ophtholmol. Vis. Sci.* 102 (1980); Michelson, "Experimental Endophthalmitis Treated with an Implantable Osmotic Minipump," 97 *Arch. Ophthalmol.* 1345 (1979); and Miki, "Intraocular Cannula for Continuous, Chronic Drug Delivery," 103 *Arch. Ophthalmol.* 712 (1985).

All of these devices, however, require the implantation of a mini-pump which must be designed and prepared to deliver a specific predetermined drug desired. These devices are large and cumbersome to attach to the eye for even a few days. They give only a slow, constant infusion, being incapable of delivering a bolus, or of delivering selectively different drugs over an intermittant time period. Furthermore, such devices depend upon the presence of a pumping pressure to prevent reflux of fluid out of the cavity into which the drug is being infused. If the pump becomes detached, either purposely or accidentally, there is no mechanism to prevent extrusion of ocular fluids, causing loss of pressure in and damage to the eye.

SUMMARY OF THE INVENTION

The invention provides an infusion cannula for infusing fluids into various cavities of the eye. The cannula comprises a tube having first and second ends and a check valve therebetween for allowing fluid flow only toward said first end. Means is provided for securing the first end within the eye, and means is provided at the second end for attaching the cannula to a fluid source. In a preferred embodiment the second end includes a hilt for receiving a tube from an infusion pump. In another embodiment the second end includes a rubber plug for receiving a hypodermic needle or similar device. The cannula may also include a compressable reservoir and/or a plurality of one-way check valves. The reservoir further may be adapted to receive a hypodermic needle directly therein.

In another embodiment, the invention relates to a method of infusing fluid into the eye, comprising the steps of providing an infusion cannula having first and second ends and a check valve therebetween to allow fluid flow only toward said first end; surgically inserting the first end of the cannula into the eye; attaching an infusion fluid source to the second end of the cannula; infusing fluid into the eye; and detaching the fluid source from the second end of the cannula, whereby the check valve will prevent escape of any fluid through the cannula.

BEST MODE OF CARRYING OUT THE INVENTION

Figure 1:
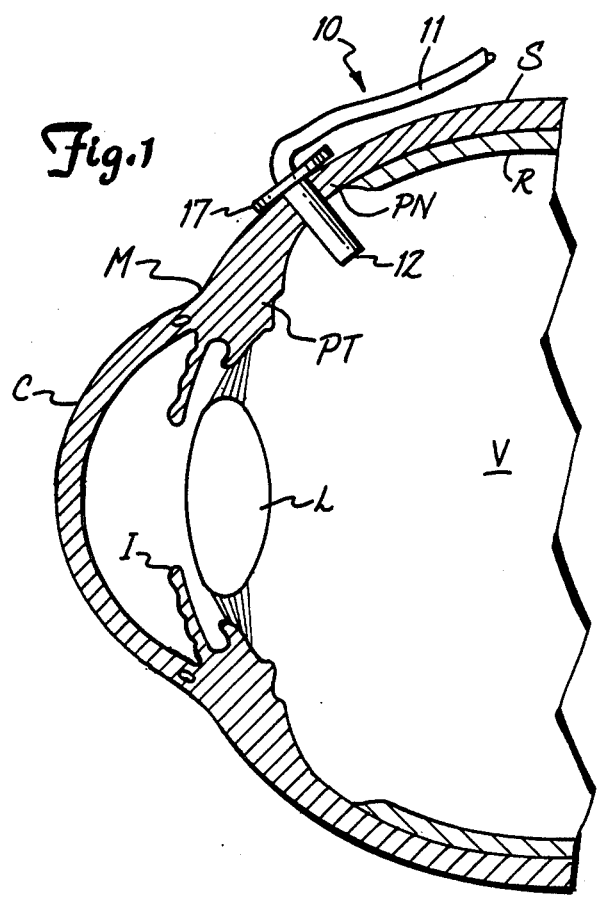
FIG. 1 is a cross-section of an eye showing a partially broken-away view of the device of the invention implanted in the eye.

FIG. 1 shows somewhat schematically a cross-section of the human eye including the device of the invention implanted therein. In that figure the cornea is designated "C"; the iris as "I", the lens as "L", the sclera as "S", the retina as "R", the pars plicata of the ciliary body as "PT", the pars plana of the ciliary body as "PN", the vitreous cavity as "V", and the limbus as "M". An infusion cannula device (10) is shown inserted through the pars plana of the ciliary body "PN" into the vitreous cavity "V".

Figure 4:
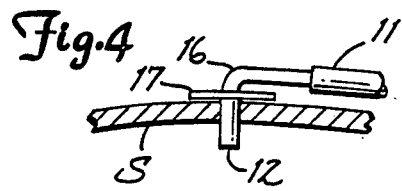
FIG. 4 is a broken-away view of another modified embodiment of the invention.
Figure 5:
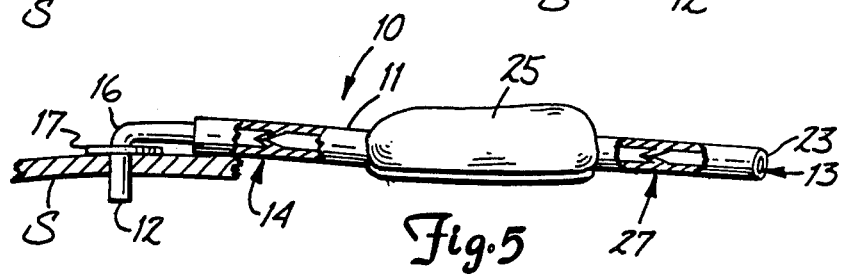
FIG. 5 is a broken-away view of yet another modified embodiment of the invention.
Figure 2:
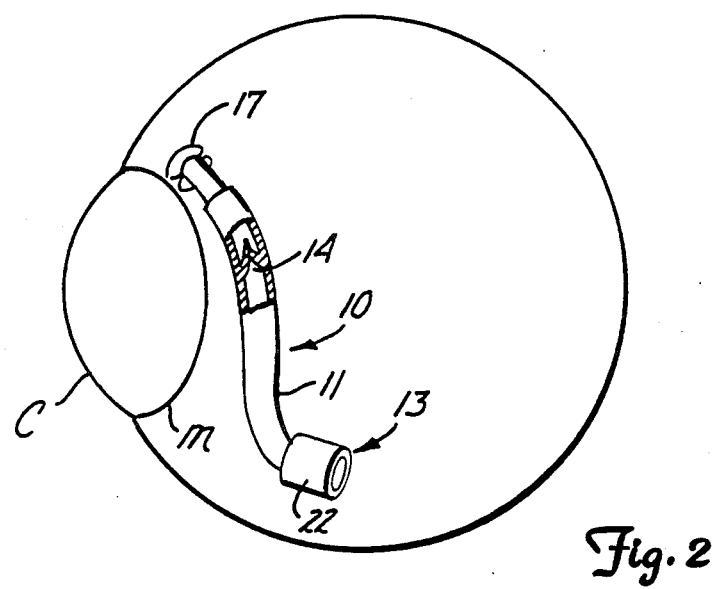
FIG. 2 is a perspective, somewhat schematic view of an eye showing an infusion device of the invention implanted therein.

A preferred embodiment of the device is shown more fully in FIG. 2. The cannula (10) includes a tube (11) having a first end (12) inserted through the pars plana "PN" of the ciliary body into the vitreous cavity "V". As shown in FIGS. 2, 4 and 5, the first end (12) may comprise a relatively rigid tube connectable to a more flexible tube (11). The rigid portion (16) facilitates implantation and affixation of the device. The second end (13) of the tube (11) includes a hilt (22) for connection to an infusion fluid source.

A one-way valve (14) is disposed within the tube between its first (12) and second (13) ends. This valve is a check valve to allow fluid flow only in a direction toward the vitreous cavity "V" of the eye. The device may further include a flange (17) which may be secured to the sclera "S" by sutures or other conventional means.

The surgical procedure for implanting the device (10) involves first opening the conjunctiva and Tenon's capsule down to bare sclera. An incision is made through the sclera into the vitreous cavity, avoiding the retina if over the pars plana or more anterior. Following this, the first end (12) is threaded through the scleral wound, and the flange (17) is secured with sutures placed in the sclera. The conjunctiva is then closed about the tube with sutures, allowing the second end (13) to come out of the conjuctiva into the cul-de-sac and exiting between the eyelids to be taped or sutured to skin of the temple.

Preferably the device is implanted through the pars plana of the ciliary body, generally about 3 mm from the limbus "M". Under appropriate circumstances, however, the device could also be implanted at the limbus or cornea into the anterior chamber, or through the retina into the vitreous cavity. The device may also be adapted to infuse fluid into any portion of the orbital spaces, subconjunctivally, subtenonally, or retrobulbularly.

Figure 3:
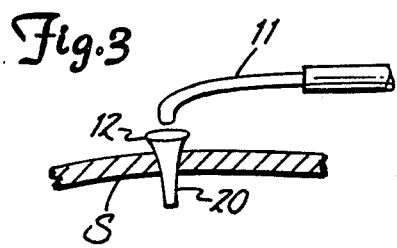
FIG. 3 is a broken-away view of a modified embodiment of the invention.

FIG. 3 shows an alternate embodiment in which a rigid trochar (20) is first implanted through the pars plana of the ciliary body, and a flexible tube is thereafter inserted through the trochar (20). The trochar (20) may then be removed, and the tube connected to the balance of the infusion cannula device (10). This technique facilitates use of entirely flexible materials, reducing the likelihood of irritation to or erosion of the conjunctiva.

For patients requiring use of the device for only a relatively short period of time (such as several days or a few weeks) the second end (13) of the device may be positioned forwardly, exiting the eye between the eyelids and temporarily affixed, for example, by adhesive tape to the temple or forehead of the patient. The second end (13) may include a hilt (22) which can be selectively connected to or disconnected from complimentary tubing from an infusion fluid source. Alternately, the second end (13) of the tube may comprise a solid rubber plug (23) adapted to receive fluid therethrough by injection from a hypodermic needle. In this embodiment, the tube may be small enough to position the second end (13) within the cul-desac of the conjunctiva. Such an embodiment would be more suited to administration of infusion fluids over longer periods of time or when the patient is not hospitalized. This embodiment also has the advantage of being more aesthetically pleasing.

FIG. 5 shows a preferred embodiment in which the device further includes a reservoir (25), and may also include a second check valve (27). This embodiment is particularly suited to long term application of the device (for example, several weeks or months). When implanted, the second end (13) of the tube, which includes a rubber plug (23) for receiving a hypodermic needle, is positioned within the cul-de-sac of the conjunctiva. When adminstration of infusion fluid is desired, the physician inserts a hypodermic needle through the rubber plug (23) and fills the reservoir (25) with infusion fluid. The reservoir itself may be attached to the sclera "S" of the eye in a position to allow convenient digital manipulation to express the infusion fluid outwardly from the reservoir toward the first end (12) of the device (10). The check valve or valves prevent reflux of the infusion fluid.

The device may be manufactured by any of a variety of well known suitable materials. Rigid portions of the device may be made from polymethylmethacrylate (PMMA) or other suitable materials such as biologically acceptable metals. The flexible portions of the tubing may be made from silicone rubber or other similar materials. The one-way check valve may be any of a variety of well known designs which need not be described in detail, but might include, by way of example, well known "duck valves."

In use, the physician may surgically implant the device of the invention, as previously described, at the appropriate location in the eye. The second end (13) of the tube (11) may be draped outwardly between the eyelids and affixed for example, to the temple by adhesive tape. When infusion treatment is desired, a suitable infusion fluid source, such as an infusion pump, may be connected to the second end (13) of the tube (11), and the appropriate fluid infused. The fluid source may then be detached from the second end, the check valve preventing escape or reflux of the fluid. After an appropriate period of time, treatment may be repeated. If long term treatment is desired, the device may be provided with the appropriate structure as previously described to allow the entire device to remain within the eye and the cul-de-sac of the conjunctiva. In either case, the device of the invention provides a means for repeatedly introducing appropriate fluids into the eye without causing repeated physical invasions of the eye. The device further provides the flexibility of varying treatment from one time to the next, both as to amount and type, without replacing or disturbing the device.

While a preferred embodiment of the present invention has been described, it should be understood that various changes, adaptations and modifications may be made therein without departing from the spirit of the invention and the scope of the appended claims.

What is claimed is:

1. An implantable infusion cannula for infusing fluids into an eye, comprising a tube having first and second ends and having a flexible portion therebetween capable of conforming to the curvature of the eye; check valve means positioned between the first and second ends for allowing fulid flow only toward the first end; means adjacent to the first end for securing the tube to an eye wall; and means at said second end for attaching the cannula to a fluid source.

2. The infusion cannula of claim 1 further comprising a compressable reservoir interposed between said check valve and said second end for receiving infusion fluid.

3. The infusion cannula of claim 1 wherein the attaching means comprises a rubber plug for receiving therethrough a hypodermic needle.

4. The infusion cannula of claim 1, wherein the securing means comprises a flange extending radially outwardly from the tube near its first end, the flange being attachable to the eye.

5. The infusion cannula of claim 1 wherein the attaching means comprises a hilt for receiving infusion tubing.

6. An implantable infusion cannula for infusing fluids into an eye, comprising a tube having first and second ends and having a flexible portion therebetween capable of conforming to the curvature of the eye; check valve means disposed within the tube between the first and second ends, compressible reservoir means interposed between said check valve means and the second end for receiving infusion fluid; means adjacent to the first end for securing the tube to an eye wall, said means including a flange extending radially outwardly of the tube adjacent its first end, the flange being attachable to the eye wall; and means at said second end for attaching the cannula to a fluid source.

7. The infusion cannula of claim 6 wherein the attaching means comprises a rubber plug for receiving therethrough a hypodermic needle.

8. Infusion cannula of claim 6 wherein the attaching means comprises a hilt for receiving infusion tubing.

9. A method of infusing fluid into an eye comprising the steps of:
providing an implantable infusion cannula having first and second ends and a flexible portion therebetween capable of conforming to the curvature of the eye and a check valve disposed within the tube between the first and second ends to allow fluid flow only toward the first end;
surgically inserting the first end of the cannula into the eye;
securing the cannula to an eye wall;
attaching an infusion fluid source to the second end of the cannula;
periodically infusing fluid into the eye; and
detaching the fluid source from the second end of the cannula, whereby the check valve will prevent reflux of fluid through the cannula.

10. The method of claim 9 wherein the insertion step includes the step of inserting the first end of the cannula through the wall of the eye into the vitreous cavity.

11. The method of claim 9 wherein the attaching step includes the step of attaching a tube to a hilt at the second end of the cannula.

12. The method of claim 9 wherein the attaching step includes the step of inserting a hypodermic needle through a rubber plug contained in the second end of the tube.

13. The method of claim 12 further comprising the step of providing a compressable reservoir in fluid communication with the tube and disposed between the check valve and said second end, the infusing step including the steps of infusing fluid into the reservoir and compressing the reservoir to infuse fluid into the eye.

14. The method of claim 9 wherein the first end of the cannula is inserted into orbital spaces outside of the vitreous cavity.

* * * * *